(12) United States Patent
Demopulos et al.

(10) Patent No.: US 8,006,700 B2
(45) Date of Patent: *Aug. 30, 2011

(54) SOFT TISSUE REPAIR SYSTEM

(76) Inventors: Gregory A. Demopulos, Mercer Island, WA (US); Scott W. Reed, Monroe, CT (US); Alan B. Bachman, Milford, CT (US); Frederick T. Karl, Newtown, CT (US); William J. Allen, Stratford, CT (US); Leland Ray Adams, Ansonia, CT (US); G. Lawrence Thatcher, Chelmsford, MA (US)

( * ) Notice: Subject to any disclaimer, the term of this patent is extended or adjusted under 35 U.S.C. 154(b) by 391 days.

This patent is subject to a terminal disclaimer.

(21) Appl. No.: 10/114,709

(22) Filed: Apr. 2, 2002

(65) Prior Publication Data
US 2002/0169477 A1  Nov. 14, 2002

Related U.S. Application Data

(63) Continuation of application No. PCT/US01/40061, filed on Feb. 7, 2001.

(60) Provisional application No. 60/180,702, filed on Feb. 7, 2000.

(51) Int. Cl.
*A61B 19/00* (2006.01)
(52) U.S. Cl. .......... 128/898; 606/213; 606/300
(58) Field of Classification Search .......... 606/215, 606/216, 214, 221, 212, 59, 64, 67, 73, 75, 606/213, 24, 300, 304, 305, 309, 321, 329, 606/314; 623/1.12; 411/479, 930, 439; 52/514.5
See application file for complete search history.

(56) References Cited

U.S. PATENT DOCUMENTS
3,176,316 A   4/1965   Bodell
(Continued)

FOREIGN PATENT DOCUMENTS
EP   0520177 A1   12/1992
(Continued)

OTHER PUBLICATIONS

Sanders, D.W., et al., "Cyclic Testing of Flexor Tendon Repairs: an In Vitro Biomechanical Study," *J. Hand Surg.* 22:1004-1010 (1997).
(Continued)

*Primary Examiner* — Gary Jackson
*Assistant Examiner* — Michael Mendoza
(74) *Attorney, Agent, or Firm* — Marcia S. Kelbon

(57) ABSTRACT

A medical fastener (18), preferably bioabsorbable, is used for repairing torn soft tissue, particularly meniscal tissue (16). The fastener (18) can have an enlarged head (22) at the proximate end to engage meniscal tissue (16) adjacent to a tear (14), and a pointed distal tip (21) at the other end to ease insertion of the fastener (18) into the meniscus (16). The shank (20) of the fastener (18) bridges across the tear (14). Opposite ends of the shank (20) are secured in the meniscal tissue (16) by a medical adhesive, preferably bioabsorbable, and preferably at locations remote from the tear (14) so as not to interfere with healing of the tear (14). The fastener (18) can have a blind bore (24) opening through the head (22) of the fastener (18) and extending through the shank (20) to a location close to the tip (21) and generally radial holes (26) communicating between the bore (24) and the exterior of the shank (20). The medical adhesive can be injected through the bore (24) for passage outward through the holes (26).

8 Claims, 4 Drawing Sheets

U.S. PATENT DOCUMENTS

| | | | |
|---|---|---|---|
| 3,716,058 A | 2/1973 | Tanner | |
| 3,833,002 A | 9/1974 | Palma | |
| 3,842,441 A | 10/1974 | Kaiser | |
| 3,960,152 A | 6/1976 | Augurt et al. | |
| 3,987,497 A | 10/1976 | Stoy et al. | |
| 3,991,766 A | 11/1976 | Schmitt et al. | |
| 4,501,029 A | 2/1985 | McMinn | |
| 4,512,038 A | 4/1985 | Alexander et al. | |
| 4,534,349 A | 8/1985 | Barrows | |
| 4,653,487 A * | 3/1987 | Maale | 606/62 |
| 4,653,489 A | 3/1987 | Tronzo | |
| 4,662,884 A | 5/1987 | Stensaas et al. | |
| 4,873,976 A | 10/1989 | Schreiber | |
| 4,976,715 A * | 12/1990 | Bays et al. | 606/77 |
| 4,979,956 A | 12/1990 | Silvestrini | |
| 5,047,030 A * | 9/1991 | Draenert | 606/65 |
| 5,061,281 A | 10/1991 | Mares et al. | |
| 5,061,283 A | 10/1991 | Silvestrini | |
| 5,102,413 A * | 4/1992 | Poddar | 606/62 |
| 5,147,362 A | 9/1992 | Goble | |
| 5,249,899 A * | 10/1993 | Wilson | 411/82 |
| 5,254,132 A | 10/1993 | Barly et al. | |
| 5,350,798 A | 9/1994 | Linden et al. | |
| 5,354,305 A | 10/1994 | Lewis et al. | |
| 5,425,766 A | 6/1995 | Bowald | |
| 5,458,636 A | 10/1995 | Brancato | |
| 5,584,859 A * | 12/1996 | Brotz | 606/228 |
| 5,612,052 A | 3/1997 | Shalaby | |
| 5,653,769 A | 8/1997 | Barly et al. | |
| 5,666,779 A * | 9/1997 | Fuchs et al. | 52/705 |
| 5,723,008 A | 3/1998 | Gordon | |
| 5,743,912 A * | 4/1998 | Lahille et al. | 606/65 |
| 5,800,407 A * | 9/1998 | Eldor | 604/264 |
| 5,800,544 A | 9/1998 | Demopulos et al. | |
| 5,811,091 A | 9/1998 | Greff et al. | |
| 5,843,084 A * | 12/1998 | Hart et al. | 606/77 |
| 5,900,245 A | 5/1999 | Sawhney et al. | |
| 5,976,127 A * | 11/1999 | Lax | 606/32 |
| 5,998,472 A | 12/1999 | Berger et al. | |
| 6,001,345 A | 12/1999 | Askill et al. | |
| 6,048,343 A | 4/2000 | Mathis et al. | |
| 6,080,192 A | 6/2000 | Demopulos et al. | |
| 6,083,244 A | 7/2000 | Lubbers et al. | |
| 6,102,947 A | 8/2000 | Gordon | |
| 6,106,556 A | 8/2000 | Demopulos et al. | |
| 6,214,012 B1 | 4/2001 | Karpman et al. | |
| 6,264,675 B1 * | 7/2001 | Brotz | 606/228 |
| 6,270,517 B1 * | 8/2001 | Brotz | 606/228 |
| 6,296,641 B2 * | 10/2001 | Burkhead et al. | 606/61 |
| 6,565,572 B2 * | 5/2003 | Chappius | 606/73 |
| 6,610,079 B1 * | 8/2003 | Li et al. | 606/232 |
| 6,620,185 B1 * | 9/2003 | Harvie et al. | 606/232 |
| 6,740,100 B2 * | 5/2004 | Demopulos et al. | 606/152 |

FOREIGN PATENT DOCUMENTS

| | | |
|---|---|---|
| SU | 566575 | 8/1977 |
| WO | WO 01/28457 A1 | 4/2001 |

OTHER PUBLICATIONS

Norris et al., "Flexor Tendon Suture Methods: a Quantitative Analysis of Suture Material within the Repair Site," *Orthopedics* 22:413-416 (1999).

Radford et al., "Immediate Strength After Suture of a Torn Anterior Cruciate Ligament," *J. Bone Joint Surg.* 76:480-484 (1994).

Lazovic et al., "Collagen Repair Not Improved by Fibrin Adhesive. Cruciate Ligament Ruptures Studied in Dogs," *Acta Orthop. Scand.* 64:583-586 (1993).

Potenza, Austin D., "Tendon Healing Within the Flexor Digital Sheath in the Dog," *The Journal of Bone and Joint Surgery* 44-A:49-64 (1962).

Allan et al., "Evaluation of Adhesive and Absorption Properties for Absorbable Tissure Adhesives," *Unpublished Work* (2000).

Shalaby et al., "Controlling the Adhesion of Polymers to Soft and Hard Tissues," *Proc. 21st Meeting, Adhesion Society*, Feb. 22-25, 1998.

Kline et al., "A Model Test Method for Evaluation of Absorbable Tissue Adhesives," *Trans. Sixth World Biuomater. Cong., III*, 1062 (2000).

Dayal et al., "The Effect of pH on Absorbable Tissue Adhesive Strengths," *Trans. Sixth World Biuomater. Cong., III*, 1070 (2000).

Hinds, et al., "A Bilaminar Elastin Patch Deployed with a Bioabsorbable Cyanoacrylate to Repair," *Trans. Sixth World Biuomater. Cong., III*, 1060 (2000).

Allan et al., "In vitro and In vivo Screening of New Compliant Absorbable Hemostatic Tissue Adhesives," *Trans. Sixth World Biuomater. Cong., III*, 318 (2000).

Flagle et al., "Absorbable Tissue Adhesives in Skin Wound Repair," *Trans. Soc. Biomater.*, 22:376 (1999).

Allan et al., "Absorbable Gel Forming Sealants/Adhesives as a Staple Adjuvant in Wound Repair," *Trans. Soc. Biomater.*, 22:374 (1999).

Flagle et al., "In vitro Evaluation of Absorbable Tissue Adhesives," *Trans. Soc. Biomater.*, 22:376 (1999).

Bionx Implants, Inc., "Bionx Implants—Meniscus Arrow," www.bionximplants.com (Internet Access Date: Oct. 15, 2002).

Mitek Products, "Mitek—Meniscal Repair System," www.jnjgateway.com (Internet Access Date Jun. 20, 2000).

Arthrotek a Biomet Company, "Arthrotek—Meniscal Staple," *Pamphlet* (2002).

Peretti et al., "Tissue Engineered Implant for Meniscus Repair," *Report* (2002).

Arthrex, "Arthrex Surgical Techniques," www.arthrex.com (Internet Access Date Jun. 20, 2000).

Sherman et al., "The Long-Term Followup of Primary Anterior Cruciate Ligament Repair. Defining a Rationale for Augmentation," *Am. J. Sports Med.* 19:243-255 (1991).

Richards, H. J., "Repair and Healing of the Divided Digital Flexor Tendon," *Injury* 12:1-12 (1980).

Becker, H., "Primary Repair of Flexor Tendons in the Hand without Immobilisation—Preliminary Report," *Hand* 10:37-47 (1978).

Silfverskiold et al., "Two New Methods of Tendon Repair: an In Vitro Evaluation of Tensile Strength and Gap Formation," *J. Hand Surg.* 18:58-65 (1993).

Strickland, J., "Flexor Tendon Repair: Indiana Method," et seq., *The Indiana Hand Center Newsletter*, 1:1-120 (1993).

"Sports, Orthopedic and Rehabilitation Medicine Associates—Torn Meniscus," www.soarmedical.com (Internet Access Date: Jun. 28, 2000).

Koukoubis, T.D., et al., "Augmentation of meniscal repairs with cyanoacrylate glue," *Journal of Biomedical Materials Research*, 29:715-720 (1995).

* cited by examiner

US 8,006,700 B2

SOFT TISSUE REPAIR SYSTEM

CROSS-REFERENCE TO RELATED APPLICATION

The present application is a continuation of International Application PCT/US01140061 filed Feb. 7, 2001 designating the United States, which claims the benefit of the filing date of Unites States Provisional Application Serial No. 60/180,702, filed on Feb. 7, 2000.

FIELD OF THE INVENTION

The present invention relates generally to systems for repairing body tissue and more specifically to systems for repairing meniscal tissue.

BACKGROUND OF THE INVENTION

Meniscal tissue in the knee may develop a longitudinal, vertical lesion sometimes referred to as a "bucket handle" lesion. It is recognized that such lesions will heal over time if the lesion is closed and stabilized. One known method for repairing a meniscus tear includes making an arthrotomy incision in the knee in order to place a suture into the inner portion of the torn meniscus, through to the outer portion. Another known procedure involves the use of a pair of long needles which contain a suture between them, and placing the two needles through the torn meniscus from the front of the knee joint exiting percutaneously the posterior area of the joint.

Another meniscal repair system, promoted by Bionx Implants, Inc., uses a fastener which is proposed to be inserted arthroscopically. The fastener has a shank, an enlarged head at one end of the shank, and one or more barbs at the other end and/or spaced along the length of the shank. The barbed end of the fastener is tapered to a point. In the Bionx system, the fastener is inserted, pointed end first, into the interior region of the meniscus adjacent to the tear. Insertion is continued until the enlarged head engages meniscal tissue. The length of the shank is selected to extend beyond the opposite side of the meniscus. The barbs are intended to prevent retraction of the fastener so that the meniscal tear is closed and the opposing sides of the tear will heal together.

SUMMARY OF THE INVENTION

The present invention provides an improved insertable surgical fastener and method for repairing torn body tissue. The improved fastener or stent preferably includes an elongated shank having an enlarged proximate head end and a pointed distal tip end. A long blind bore extends through the head end and shank to a location close to the tip. Transverse holes communicate between the blind bore and the exterior of the shank.

The improved fastener can be inserted into the interior region of a meniscus tear to be repaired. With the fastener held in position with the head end engaging the meniscus and holding the lesion closed and stabilized, medical adhesive is inserted into the bore through the head end and flows outward through the transverse holes. Preferably the adhesive sets almost immediately for stabilizing the now closed lesion without interfering with healing. In alternative embodiments, adhesive may be injected from the exterior of the stent to make the adhesive bond between the stent and adjacent tissue.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention is used to repair soft tissue, particularly a meniscal tear.

Figure 1:
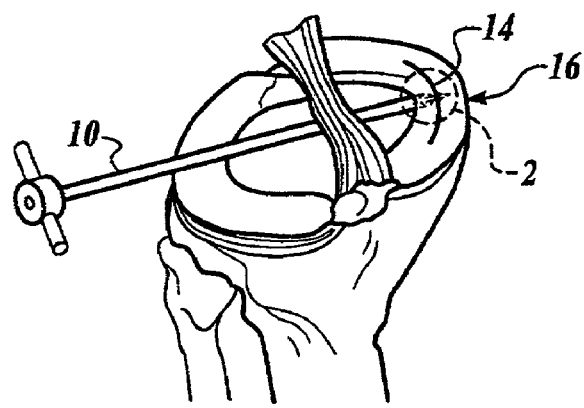
FIG. 1 (prior art) is a diagrammatic top perspective of a torn meniscus and adjacent anatomy, showing a known device for repairing a meniscal tear.
Figure 2:
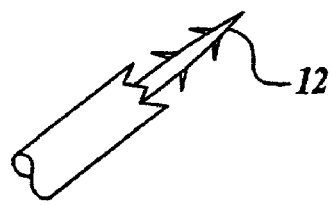
FIG. 2 (prior art) is an enlarged fragmentary perspective of part of the known system represented in FIG. 1, including a barbed fastener.
Figure 3:
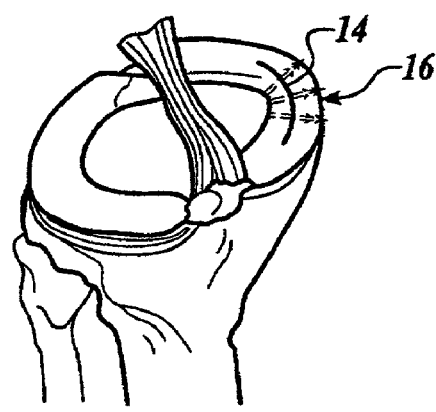
FIG. 3 (prior art) is a top perspective corresponding to FIG. 1 showing a meniscal tear repaired in accordance with the known system.
Figure 4A:
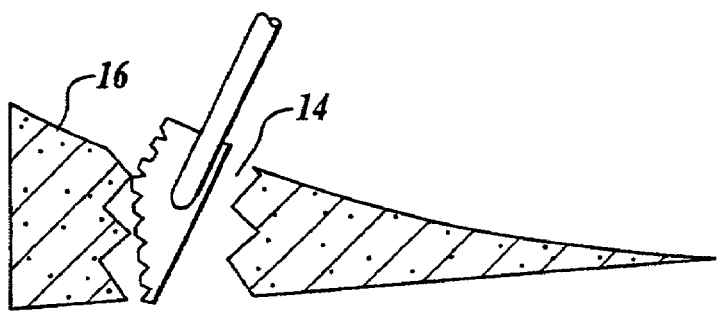
FIGS. 4A through 4E (prior art) are corresponding diagrammatic sectional views illustrating repair of a meniscal tear in accordance with the known system.
Figure 4B:
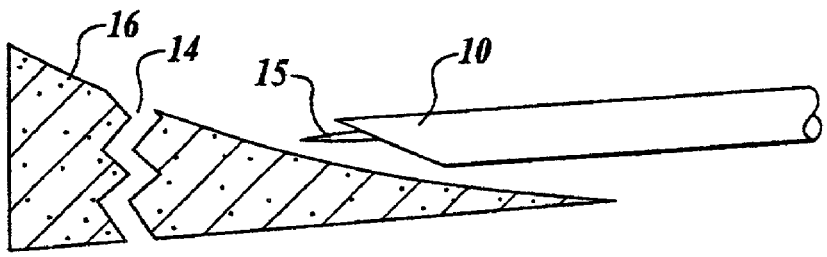
Figure 4C:
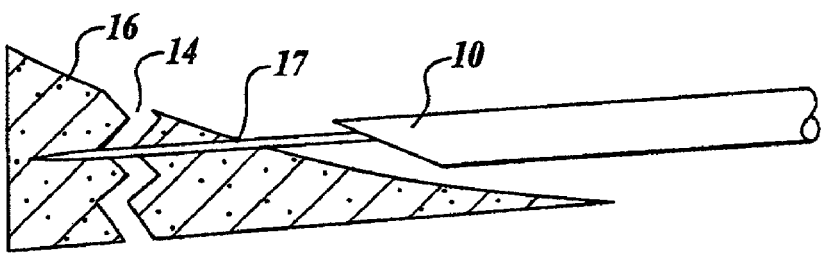
Figure 4D:
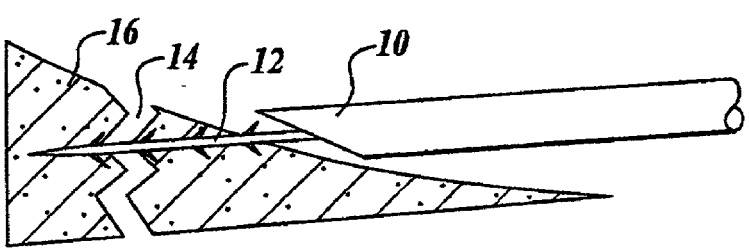
Figure 4E:
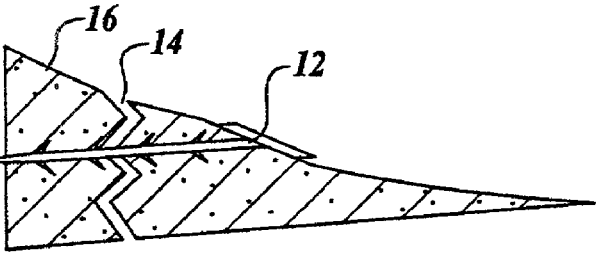

FIGS. 1-4 illustrate a known prior art system promoted by Bionx Implants, Inc., which is the subject of Schreiber U.S. Pat. No. 4,873,976. The Schreiber-Bionx system uses a special applicator tube 10 positioned for insertion of a fastener 12 (FIG. 2) with its barbed shank extending across a tear 14 in the medial meniscus 16. FIG. 3 shows a "repaired" tear in which three such fasteners 12 have been inserted. FIGS. 4A-4E illustrate one procedure recommended by Bionx Implants, Inc., for using Schreiber-type fasteners to repair a meniscal tear. More specifically, the tear or rupture 14 of the meniscus 16 is freshened and reduced with an arthroscopic rasp as represented in FIG. 4A. With reference to FIG. 4B, for posterior lesions an "arrow" 15 is placed at the most posterior area first, whereas for medial lesions the arrow is placed at the middle of the tear first. A cannula 10 is inserted with a blunt obturator inside. The obturator is removed while the meniscus is maintained in its reduced state with the cannula. The exact position of the cannula is to be maintained during the entire procedure by pressing it against the meniscus. With reference to FIG. 4C, a channel is made through the meniscus into the joint capsule with a special needle 17. Typically, irrigation fluid will flood the area during the initial stages of the procedure, and it is recommended that the fluid be turned off prior to retracting the needle. The fastener is then pushed to the surface of the meniscus with the obturator. With reference to FIG. 4D, a piston mounted on a reciprocating instrument run by air pressure or electricity uses the obturator as a manual driver to hammer the implant fastener 12 into the meniscus. With reference to FIG. 4E, the T-shaped head is pushed into the groove formed during driving on the surface of the meniscus. The cannula is shifted to a new position and the procedure repeated again until the desired number of implant fasteners has closed the meniscal tear. Fasteners are recommended to be separated by five to ten millimeters, and may be provided in different lengths, depending on the location of the tear.

Thus, the Schreiber-Bionx system relies on the barbs of the fastener to prevent it from becoming dislodged and possibly allowing the tear to reopen or at least not be held together sufficiently to heal together as completely or reliably as otherwise might occur.

Figure 5:
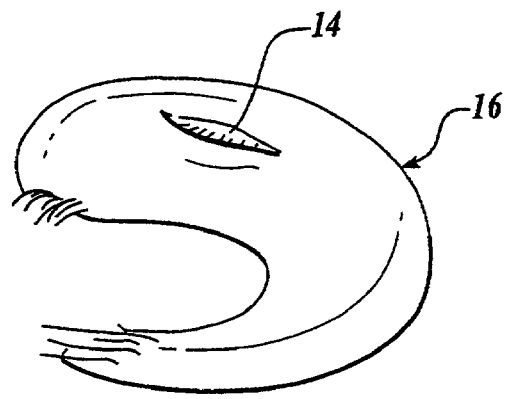
FIG. 5 is an enlarged perspective of a torn medial meniscus of the type that can be repaired in accordance with the system of the present invention.
Figure 6:
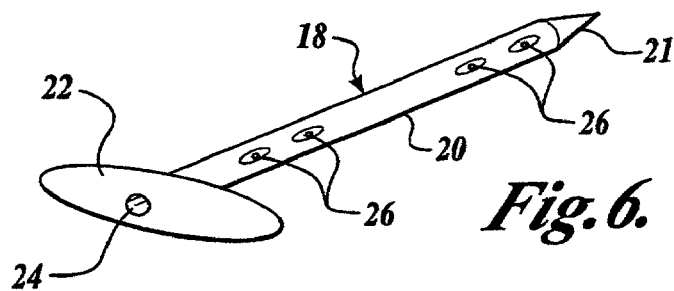
FIG. 6 is an enlarged top perspective of an improved fastener or stent in accordance with the present invention.

The present invention provides an improved insertable fastener and method for repairing torn body tissue. FIG. 5 illustrates diagrammatically a representative tear, namely, a tear 14 in the medial meniscus 16. In one embodiment of the invention, a fastener or "stent" 18 of the type shown in FIG. 6 is used. Stent 18 includes a shank 20 which preferably is of cylindrical cross section but which could be of square, rectangular, octagonal, or oval cross section. A distal tip end 21 of the shank is tapered to a point. A proximate head end 22 of the shank is enlarged. A long blind bore 24 extends through the head end 22 and shank 18 to a location close to the tip end 21. Transverse holes 26 communicate between the blind bore and the exterior of the shank.

Figure 7:
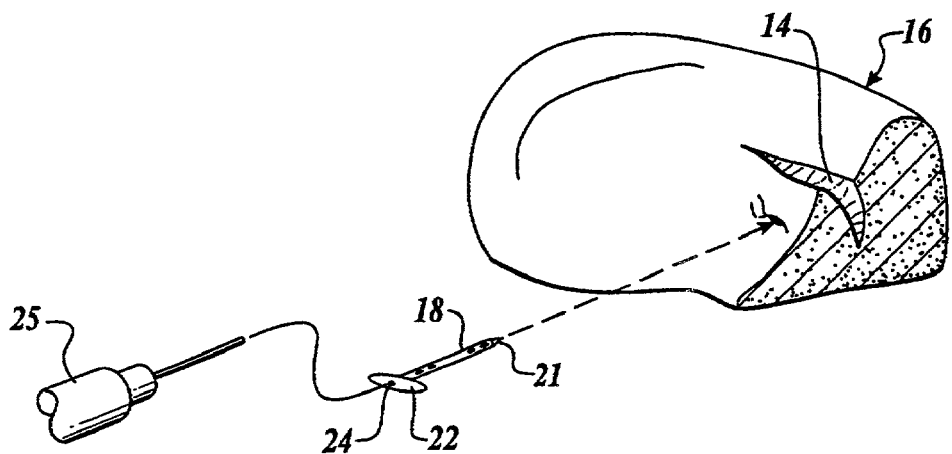
FIG. 7 is an enlarged diagrammatic perspective of a tear of the type shown in FIG. 5 and fastener of the type shown in FIG. 6 illustrating how the fastener is used for repairing the tear.

With reference to FIG. 7, the tear site 14 can be prepared conventionally, i.e., by freshening the torn area with an arthroscopic rasp. Stent 18 is inserted adjacent to the tear site 14 in a generally horizontal direction, transversely of the vertical tear. This can be done arthroscopically through a cannula. A pusher rod may be used to advance the stent, and can have a releasable grasper to assist in positioning the stent. While barbs may be provided along the shank, it is preferred that the shank be smooth and of uniform cross section for minimal trauma to undamaged tissue through which the shank is inserted. Insertion of the shank is limited by the enlarged head 22.

Preferably the interior surface (hidden from the viewer in FIGS. 6 and 7) of the enlarged head 22 is flat for firmly engaging in the meniscal tissue. Such head also can be oval with its major axis extending horizontally for maximum surface area of engagement with the meniscal tissue, but without projecting unduly in a vertical direction which could be abrasive to surrounding tissue or bone. The exterior surface (the surface closest to the viewer in FIGS. 6 and 7) can be slightly inclined and/or curved to at least approximate the surface of the meniscal tissue in the area of the embedded head.

As indicated diagrammatically in FIG. 7, with the stent inserted in a position to close the tear 14, a medical adhesive is injected through the open end of the bore 24, such as by a syringe 25, to pass through such bore and outward through the openings 26. The adhesive sets quickly and adheres to the meniscal tissue for maintaining the stent in a position closing the tear 14.

Preferably the stent will be sufficiently dimensionally stable that it will not bend or deflect substantially as it is inserted, nor elongate or stretch which could alter the abutting relationship of opposite sides of the tear and interfere with healing. However, the stent can be somewhat flexible in a transverse direction so as not to interfere with normal functioning of the repaired tissue. This may require that the stent, particularly the shank, be narrow. If too stiff or too large, abrasion could occur in the area of the shank of the stent. For the same reason, it is believed that the stent should not have exposed sharp edges.

Figure 8:
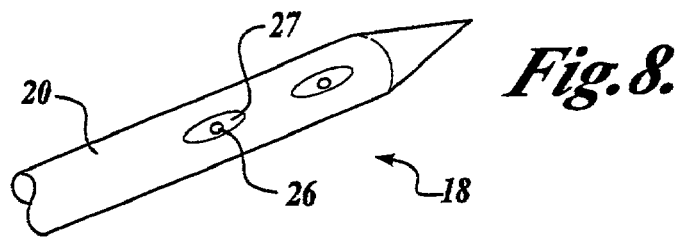
FIG. 8 is a top perspective of an alternative fastener usable in a system in accordance with the present invention.
Figure 9:
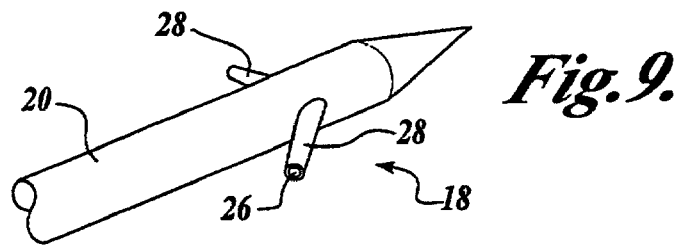
FIG. 9 is a top perspective of another fastener usable in a system in accordance with the present invention.

The viscosity of the adhesive and size and location of the transverse holes are somewhat related. It is envisioned that such holes should be provided at least in opposite sides of the shank 20 of the stent 18 for adhering to surrounding tissue. Nevertheless, the adhesive should not be so fluid nor the transverse holes 26 so large that an excess quantity of the adhesive is injected, which could interfere with the healing process (e.g., the revascularization and/or neovascularization of the repair site). It may be preferable to position the holes toward the opposite ends of the stent shank, or at least away from the area expected to be adjacent to the tear, to prevent the adhesive from flowing between the opposite faces of the tear. For example, in the embodiment of FIG. 6 the holes 26 are located at opposite end portions of the shank 20 but not in the central portion which is positioned to bridge across the tear. Also, the exit holes could be located in sockets or depressions 27 formed in the exterior of the stent shank (FIG. 8) if required to reliably and uniformly disperse the adhesive over the surface of the stent. Another possibility is to use barbs 28 on the stent shank 20 with openings at their tips or free ends (FIG. 9) and supply adhesive under sufficient pressure to penetrate surrounding tissue.

It is envisioned that the adhesive can be of the general type described in U.S. Pat. No. 5,350,798 of Linden et al. or a variant. Such an adhesive is, in general, a polymer gel and, more specifically, a cyanoacrylate polymer. Modified gels are described in U.S. Pat. Nos. 5,714,159 and 5,612,052 of Shalaby.

At the time of injection, preferably the adhesive flows freely without high adhesive properties relative to the tissue being repaired, but will thereafter set quickly and secure the sides of the tear in the desired abutting relationship. In the currently preferred embodiment, the adhesive will set within about 10 seconds to a condition of high shear strength and substantial rigidity, but not so rigid as to crack in the area of the shank if it flexes slightly during normal use of the joint. The adhesive may inherently have disinfectant characteristics and/or may be coated or impregnated with a compound having disinfectant characteristics. Alternatively or additionally, the adhesive and/or stent may serve as a delivery system for drugs and/or agents and/or factors to promote healing and/or growth. Both the stent and the adhesive preferably are bioabsorbable, but over a sufficiently long length of time that full healing of the tear occurs. In the case of a normal meniscal tear, the adhesive-stent combination should maintain full strength for approximately eight to twelve weeks and then degrade as the meniscus heals further.

Figure 10:
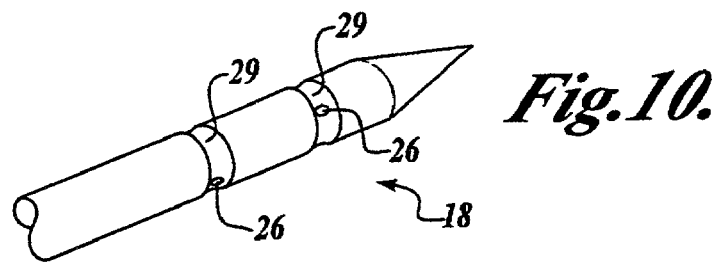
FIG. 10 is a top perspective of another fastener usable in a system in accordance with the present invention.
Figure 11:
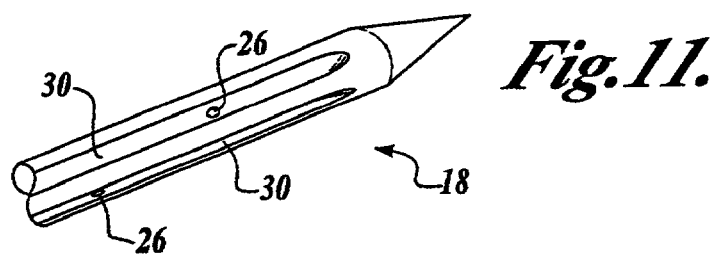
FIG. 11 is a top perspective of another fastener usable in a system in accordance with the present invention.
Figure 12:
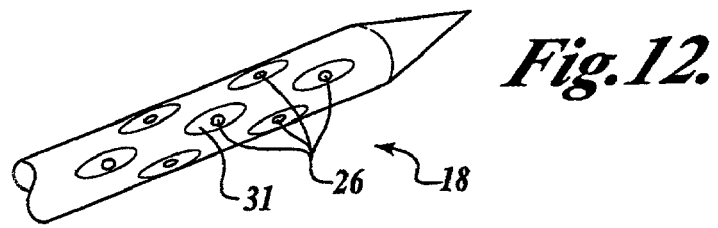
FIG. 12 is a top perspective of another fastener usable in a system in accordance with the present invention.
Figure 13:
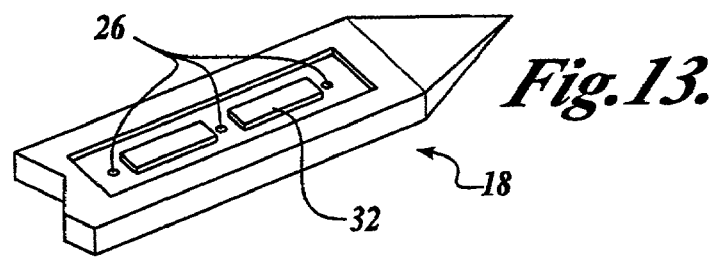
FIG. 13 is a top perspective of another fastener usable in a system in accordance with the present invention.

While the preferred characteristics of the invention have been described and illustrated, it will be appreciated that various changes can be made therein without departing from the spirit and scope of the invention. For example, while the preferred manner of delivery of the adhesive is through a bore of the stent, in another embodiment the adhesive could be injected by syringe from the exterior of the meniscus into the area of an inserted stent. Such a stent could have circumferential grooves 29 (FIG. 10) and/or longitudinal grooves 30 (FIG. 11) or a pattern of depressions 31 (FIG. 12) to increase the surface area of the stent and tissue through which it has been inserted and, if desired, the syringe could be withdrawn as the adhesive is injected to form a pattern of adhesive penetrating into surrounding tissue. In such a case, the shank of the stent could be flat (FIG. 13) with a pattern of grooves 32 in its opposite sides, but preferably the stent still would have a sharpened or pointed leading end for ease of insertion and an enlarged end to limit the degree of insertion of the stent into the tissue. Nevertheless, without an enlarged end, the stent could be held in position for a period sufficient to allow the adhesive to be injected and to set for securing the torn tissue in an abutting relationship for promoting healing. In either instance, i.e., internal or external application of the adhesive, preferably the amount of adhesive used will be metered for consistency in the adhesive properties and to prevent an insufficient or excessive quantity of adhesive from being used adjacent to the stent. The exterior surface of the meniscus at the tear site could be further stabilized and protected by a film or patch using the same or a similar adhesive.

The embodiment of the invention in which an exclusive property or privilege is claimed are defined as follows:

1. A method of repairing a tear in soft tissue, comprising:
    inserting an elongated stent having a nonthreaded shank to bridge between opposite sides of a soft tissue tear, in which the elongated shank defines an internal passage extending generally longitudinally through the shank and a plurality of holes communicating between the passage and a plurality of recesses defined in an exterior of the shank; and
    applying an adhesive on a longitudinal portion of the shank of the stent at each of the opposite sides of the tear to hold the soft tissue on each side of the tear together during healing of the tear, wherein the adhesive is applied by flowing the adhesive through the passage and the holes into the recesses in the exterior of the shank.

2. The method of claim 1, in which the shank has a central portion located to bridge across the tear and opposite end portions adjacent to the central portion, the holes being located in the opposite end portions for expelling adhesive at locations remote from the tear.

3. The method of claim 1, in which the stent includes an enlarged head at one end of the shank for engaging against soft tissue in proximity to one side of the tear, the internal passage opening through the head.

4. A method of repairing a tear in soft tissue, comprising:
    nonthreadedly inserting an elongated stent to bridge between opposite sides of a soft tissue tear, the stent having a proximal end defining an enlarged head and a nonthreaded elongated shank defining a distal tip, the shank defining a surface adapted to include a plurality of recesses to receive an adhesive at least on a distal portion of the shank, the stent being inserted such that the enlarged head engages the soft tissue in proximity to one side of the tear;
    applying an adhesive to at least a longitudinal distal portion of the shank, the stent and adhesive holding the soft tissue on each side of the tear together during healing of the tear, in which the shank defines an internal passage extending generally longitudinally through the shank and a plurality of holes communicating between the passage and the plurality of recesses on an exterior surface of the shank; and
    flowing the applied adhesive through the passage and the holes into the recesses in the exterior surface of the shank.

5. The method of claim 4, in which the holes are located within a proximal portion of the shank and within the distal portion of the shank for expelling applied adhesive at locations remote from the tear.

6. A method of repairing a tear in soft tissue, comprising:
    inserting an elongated stent to bridge between opposite sides of a soft tissue tear, in which the stent includes an elongated shank and the elongated shank defines an internal passage extending generally longitudinally through the shank and a plurality of holes communicating between the passage and a plurality of recesses defined in an exterior of the shank;
    applying an adhesive into the passage; and
    flowing the applied adhesive through the passage and the holes into the recesses in the exterior of the shank to hold the stent within the soft tissue during healing of the tear.

7. The method of claim 6, wherein the stent is retained in position during healing by the applied adhesive on at least one side of the soft tissue tear and an enlarged head defined by an end of the stent on an opposite side of the soft tissue tear.

8. The method of claim 6, wherein adhesive is applied on a longitudinal portion of the shank of the stem at each of the opposite sides of the tear to hold the soft tissue on each side of the tear together during healing of the tear.

* * * * *

UNITED STATES PATENT AND TRADEMARK OFFICE
CERTIFICATE OF CORRECTION

PATENT NO.       : 8,006,700 B2
APPLICATION NO.  : 10/114709
DATED            : August 30, 2011
INVENTOR(S)      : Demopulos et al.

It is certified that error appears in the above-identified patent and that said Letters Patent is hereby corrected as shown below:

| COLUMN | LINE | ERROR |
|---|---|---|
| 1 | 7 | "Application PCT/US01140061" should read --Application PCT/US01/40061-- |
| 6 | 38 | "of the stem" should read --of the stent-- |

Signed and Sealed this
Eleventh Day of October, 2011

David J. Kappos
*Director of the United States Patent and Trademark Office*